(12) United States Patent
Wang (10) Patent No.: US 11,737,945 B2
(45) Date of Patent: Aug. 29, 2023

(54) WRIST JOINT ACTUATING STRUCTURE OF HAND REHABILITATION DEVICE

(71) Applicant: YONG TAI GLOBAL CO., LTD., Tainan (TW)

(72) Inventor: Tseng-Chiu Wang, Tainan (TW)

(73) Assignee: Yong Tai Global Co., Ltd., Tainan (TW)

(*) Notice: Subject to any disclaimer, the term of this patent is extended or adjusted under 35 U.S.C. 154(b) by 385 days.

(21) Appl. No.: 17/071,254

(22) Filed: Oct. 15, 2020

(65) Prior Publication Data

US 2022/0117824 A1 Apr. 21, 2022

(51) Int. Cl.
*A61H 1/02* (2006.01)
*A61F 5/01* (2006.01)

(52) U.S. Cl.
CPC ........... *A61H 1/0288* (2013.01); *A61F 5/013* (2013.01); *A61H 2201/1207* (2013.01); *A61H 2201/1418* (2013.01); *A61H 2201/50* (2013.01)

(58) Field of Classification Search
CPC ...... A61H 1/0288; A61H 1/0285; A61H 1/00; A61H 1/0274; A61H 2201/1418; A61H 2201/50; A61H 2201/1638; A61H 2201/165; A61H 2201/1635; A61F 5/013; A61F 5/0102; A61F 2005/0155; A61F 2005/0167; A61F 2/585; A61F 2/583; A61F 2/54; A61F 2/581; A61F 2002/503; B25J 13/02

See application file for complete search history.

(56) References Cited

U.S. PATENT DOCUMENTS

| | | | |
|---|---|---|---|
| 1,504,121 A * | 8/1924 | Harris | A61F 2/54 623/60 |
| 3,756,222 A * | 9/1973 | Ketchum | A61H 1/0288 601/40 |
| 3,944,220 A * | 3/1976 | Fasano | A63B 21/0552 482/47 |

(Continued)

FOREIGN PATENT DOCUMENTS

| | | | | |
|---|---|---|---|---|
| CN | 107361994 A | * | 11/2017 | ........... A61H 1/0218 |
| CN | 109223442 A | * | 1/2019 | ........... A61H 1/0288 |

(Continued)

*Primary Examiner* — Justine R Yu
*Assistant Examiner* — Kelsey E Baller
(74) *Attorney, Agent, or Firm* — Rosenberg Klein & Lee (57) ABSTRACT

A wrist joint actuating structure of a hand rehabilitation device includes a palm orthosis body, a forearm orthosis body and a joint unit. The palm orthosis body includes a plurality of finger support rods and a thumb support rod. The joint unit is a universal joint and is connected between the palm orthosis body and the forearm orthosis body. The palm orthosis body can be turned an angle relative to the forearm orthosis body through actuation of the joint unit according to the bending degree of a user's wrist joint. A tension adjustment unit includes elastic members connected to the finger support rods and the thumb support rod. According to the different stretching tensions required by the fingers or the thumb for rehabilitation, the respective lengths of the other ends of the elastic members to be pressed by a fixing seat are adjustable, so as to adjust different stretching tensions.

8 Claims, 9 Drawing Sheets

(56) References Cited

U.S. PATENT DOCUMENTS

| | | | | |
|---|---|---|---|---|
| 4,765,320 | A * | 8/1988 | Lindemann | A61F 5/0118 |
| | | | | D24/190 |
| 8,491,447 | B1 * | 7/2013 | Koranic | A63B 23/16 |
| | | | | 482/44 |
| 10,646,749 | B1 * | 5/2020 | Williams | A63B 23/16 |
| 2006/0211964 | A1 * | 9/2006 | Farrell | A61F 5/05866 |
| | | | | 602/5 |
| 2009/0149790 | A1 * | 6/2009 | Farrell | A61F 5/0118 |
| | | | | 602/20 |
| 2015/0374575 | A1 * | 12/2015 | Kamper | A61F 5/013 |
| | | | | 601/40 |
| 2016/0361179 | A1 * | 12/2016 | Mateus Dias Quinaz | |
| | | | | A61F 2/72 |
| 2019/0358074 | A1 * | 11/2019 | Zelik | F16D 13/58 |
| 2021/0161696 | A1 * | 6/2021 | Ewaldsson | A61H 1/0288 |
| 2022/0287853 | A1 * | 9/2022 | Ren | B25J 13/088 |

FOREIGN PATENT DOCUMENTS

| | | | | |
|---|---|---|---|---|
| TW | I541011 | B * | 9/2014 | A61H 1/0288 |
| TW | M516411 | U | 2/2016 | |
| TW | I541011 | B | 7/2016 | |

* cited by examiner

WRIST JOINT ACTUATING STRUCTURE OF HAND REHABILITATION DEVICE

FIELD OF THE INVENTION

The present invention relates to a hand rehabilitation device that can adjust the angle between a palm orthosis body and a forearm orthosis body according to the degree of bending of the wrist joint of a different user.

BACKGROUND OF THE INVENTION

As is known, in the case of damage to the joint tissues subsequent to stroke, surgery or traumas, the normal functionality of the hand, fingers, or the wrist may be altered, with both physical and psychological consequences. In general, it is necessary to use a hand rehabilitation device for rehabilitation.

Taiwan Patent Publication No. 1541011 discloses a hand rehabilitation device, published on Jul. 11, 2016. The hand rehabilitation device includes a palm-shaped plate and a forearm fixing plate. The palm-shaped plate and the forearm fixing plate are connected to each other to form an included angle. The top and one side of the palm-shaped plate are provided with five rods and five finger sleeves for receiving the user's fingers. One end of a pulling rope is connected to each finger sleeve, and the other end of the pulling rope is inserted through a guide groove of each rod and a guide collar and then secured to a collection collar. One end of a connecting rope is fixed to the collection collar. An upper arm fixing plate is provided with a pulling rope adjustment assembly. The other end of the connecting rope is fixed to the pulling rope adjustment assembly. The upper arm fixing plate is attached to the upper arm. The forearm fixing plate is attached to the forearm. All the pulling ropes can be pulled to be tightened or loosened by moving the upper arm or using the other hand to pull the connecting rope, thereby enabling the five fingers to stretch or bend for rehabilitation.

In the above-mentioned patent, the forearm fixing plate and the palm-shaped plate are fixed as a whole, and an included angle between the forearm fixing plate and the palm-shaped plate is less than 180 degrees. However, the included angle is a fixed angle and cannot be adjusted according to the bending angle of the wrist joint of a different user. By pulling a handle fixed to the other end of the connecting rope, all the pulling ropes are pulled to be tightened or loosened, enabling the five fingers to stretch or bend for rehabilitation. Because all the pulling ropes are pulled at a time to adjust the five fingers for rehabilitation, it is unable to adjust different elastic forces for different fingers separately according to the bending degree of different fingers, so it is not ideal for use.

In addition, Taiwan Utility Model Publication No. M516411 discloses a hand dynamic orthosis, published on Feb. 1, 2016. The hand dynamic orthosis includes an orthosis plate. The orthosis plate is provided with a finger traction elastic assembly corresponding to each finger of the human body. Each finger traction elastic assembly includes an elastic line. One end of the elastic line is defined as an elastic positioning end positioned on the surface of the orthosis plate, and the other end of the elastic line is extended with a set length and provided with a strap. After the orthosis plate is worn on the patient's hand, when the finger sleeved with the finger traction elastic assembly is to bend and stretch to pull the elastic positioning end at the other end of the finger traction elastic assembly in an elastic manner, so as to form corresponding elastic traction to bend and stretch the proximal and distal joints of the patient's finger for dynamic rehabilitation of the hand.

In the above-mentioned patent, the orthosis plate includes a palm portion and a wrist portion that are integrally formed. Both the palm portion and the wrist portion are fixed and integrated, and they cannot be adjusted according to the bending angle of the wrist joint of a different user. After the orthosis plate is worn on the patient's hand, when the finger tied to one end of the elastic line of the finger traction elastic assembly is to bend and stretch, the other end of the elastic line of the finger traction elastic assembly will form the elastic traction function for rehabilitation. It can be installed in accordance with the different conditions of the proximal and distal joints of the patient's finger. Besides, in various situations during the training, through an elastic coil (spring), the relative elasticity is adjusted for better rehabilitation. Because the elasticity of the general spring is relatively large, it is not suitable for patients whose fingers cannot be controlled to perform fine adjustment. Moreover, due to the excessive force of the spring, the patient's fingers cannot move at all. It is difficult to achieve the effects of training and rehabilitation. The adjustment of the elasticity of the spring is limited. If it is required for small elasticity, a spring with few coils and a small diameter is replaced. Therefore, it is quite troublesome and time-consuming to disassemble and replace the spring.

SUMMARY OF THE INVENTION

In view of the shortcomings of the prior art, the primary object of the present invention is to provide a wrist joint actuating structure of a hand rehabilitation device, comprising a palm orthosis body, a forearm orthosis body and a joint unit. The palm orthosis body includes a plurality of adjustable finger support rods and an adjustable thumb support rod. The joint unit is a universal joint. The joint unit is connected between the palm orthosis body and the forearm orthosis body. The palm orthosis body can be turned an angle relative to the forearm orthosis body through actuation of the joint unit.

Preferably, the palm orthosis body includes a first connecting portion. The forearm orthosis body includes a second connecting portion. The joint unit includes a first actuating member and a second actuating member. The first actuating member is arranged on the first connecting portion. The second actuating member is arranged on the second connecting portion. The first actuating member is movable relative to the second actuating member.

Preferably, the joint unit further includes a lock nut. The first actuating member is a ball head. The second actuating member is a ball socket. An opening of the second actuating member is provided with a threaded tightening portion. The lock nut is movably sleeved onto the first connecting portion and is screwed to the tightening portion to secure the ball head in the ball socket.

Preferably, a periphery of the tightening portion is formed with at least one slit to increase a shrinkage allowance of the tightening portion.

Preferably, the wrist joint actuating structure of the hand rehabilitation device further comprises a tension adjustment unit. The forearm orthosis body further includes a fixing seat. The tension adjustment unit includes a plurality of elastic members. First ends of the elastic members are connected to the finger support rods and the thumb support rod, respectively. Second ends of the elastic members are secured to the fixing seat. The elastic members are adjustable to generate different stretching tensions by adjusting respective lengths of the second ends of the elastic members to be secured to the fixing seat.

Preferably, the fixing seat has a pressing region. The fixing seat is pivotally connected with a plurality of pressing blocks. Each pressing block has a pulling portion and an eccentric cam portion. The pulling portion is pulled to pivot the eccentric cam portion so that the eccentric cam portion is moved to the pressing region for securing the second ends of the elastic members. The second ends of the elastic members can be adjusted for adjusting the respective lengths of the second ends of the elastic members to be pressed by the pressing blocks so as to generate the different stretching tensions.

Preferably, the finger support rods each have at least one perforation. The first ends of the elastic members are inserted through the perforations of the finger support rods and connected to distal ends of the finger support rods, respectively.

Preferably, the angle is between −30° and +60°.

Preferably, the palm orthosis body is provided with a plurality of first fixing portions. A plurality of adjustment seats are connected to the first fixing portions, respectively. The finger support rods are connected to the adjustment seats, respectively. Finger sleeves are connected to the respective distal ends of the finger support rods.

Preferably, a swing plate is pivotally connected to one side of the palm orthosis body. The swing plate is provided with a second fixing portion. The thumb support rod is connected to the second fixing portion. A finger sleeve is connected to a distal end of the thumb support rod.

The above technical features have the following advantages:

1. The joint unit is a universal joint. The palm orthosis body can be turned an angle relative to the forearm orthosis body through actuation of the joint unit according to the bending degree of the user's wrist joint.

2. The respective lengths of the second ends of the elastic members to be pressed by the pressing blocks are adjustable, so that the different elastic members produce different degrees of elasticity, that is, the elasticity of the respective elastic members can be adjusted according to the different stretching tensions required by the fingers or the thumb for rehabilitation.

DETAILED DESCRIPTION OF THE PREFERRED EMBODIMENTS

Embodiments of the present invention will now be described, by way of example only, with reference to the accompanying drawings.

Figure 1:
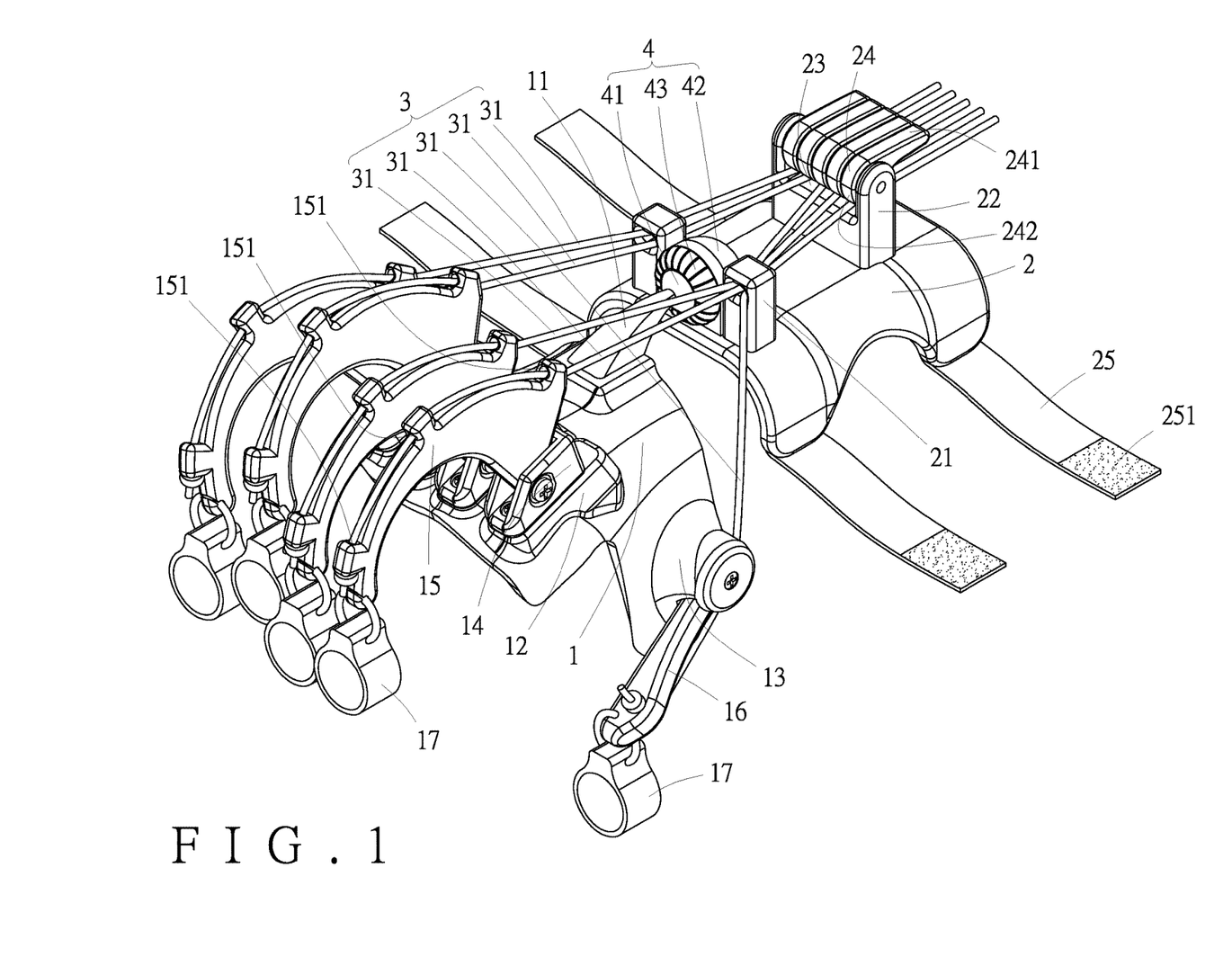
FIG. 1 is a perspective view according to a first embodiment of the present invention.
Figure 2:
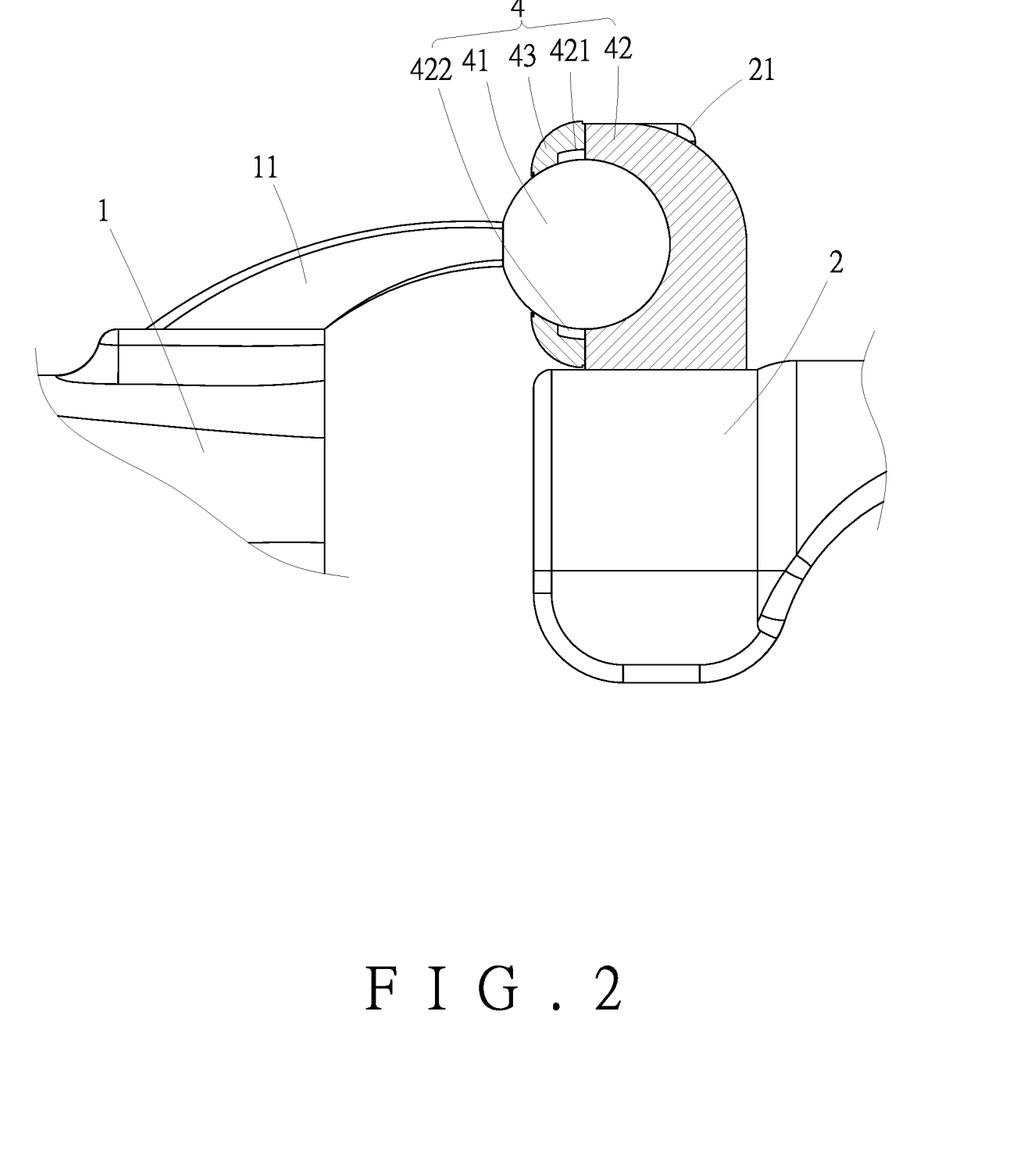
FIG. 2 is a cross-sectional view of the joint unit according to the first embodiment of the present invention.

As shown in FIG. 1 and FIG. 2, a wrist joint actuating structure of a hand rehabilitation device according to a first embodiment of the present invention comprises a palm orthosis body (1), a forearm orthosis body (2), a tension adjustment unit (3), and a joint unit (4).

One end of the palm orthosis body (1) is provided with a first connecting portion (11). The other end of the palm orthosis body (1) is provided with a plurality of first fixing portions (12) and a second fixing portion (13). A plurality of adjustment seats (14) are connected to the first fixing portions (12), respectively. The adjustment seats (14) can be moved and adjusted forward and backward relative to the corresponding first fixing portions (12), respectively. A plurality of finger support rods (15) are connected to the adjustment seats (14), respectively. The finger support rods (15) can be turned and adjusted up and down relative to the corresponding adjustment seats (14), respectively. The finger support rods (15) each have at least one perforation (151). A thumb support rod (16) is connected to the second fixing portion (13). The thumb support rod (16) can be turned and adjusted up and down relative to the second fixing portion (13). Finger sleeves (17) are connected to the respective distal ends of the finger support rods (15) and the thumb support rod (16) for a user's fingers to be inserted and positioned in the finger sleeves (17).

Figure 3:
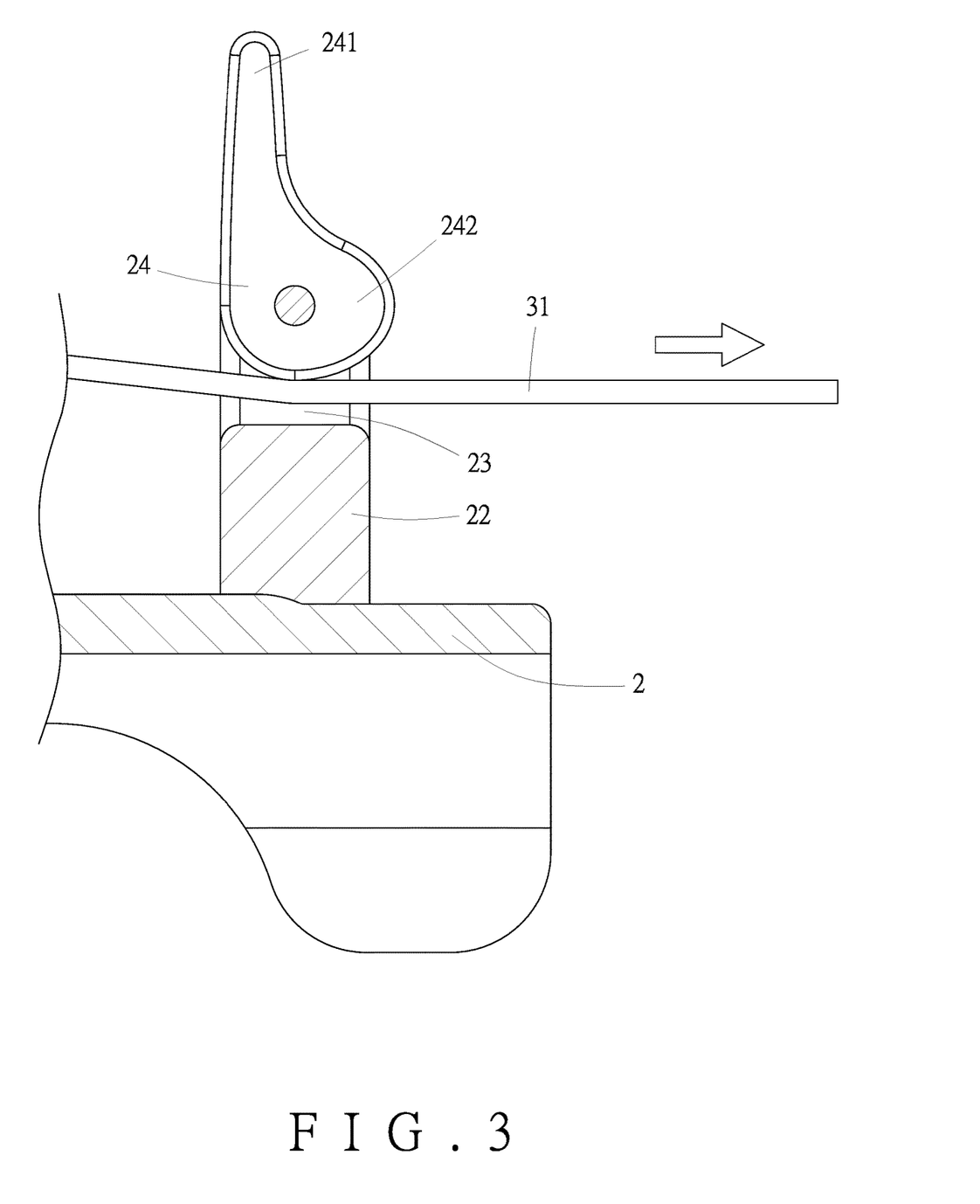
FIG. 3 is a schematic view illustrating the elastic member passing through the pressing region according to the first embodiment of the present invention.

The forearm orthosis body (2) includes a second connecting portion (21). The forearm orthosis body (2) further includes a fixing seat (22). The fixing seat (22) has a pressing region (23). The fixing seat (22) is pivotally connected with a plurality of pressing blocks (24). As shown in FIG. 3, each pressing block (24) has a pulling portion (241) and an eccentric cam portion (242). By pulling the pulling portion (241) to pivot the eccentric cam portion (242), the eccentric cam portion (242) is moved to the pressing region (23). Two sides of the forearm orthosis body (2) are provided with fastening straps (25). The fastening straps (25) are secured with a hook-and-loop tape (251).

Figure 4:
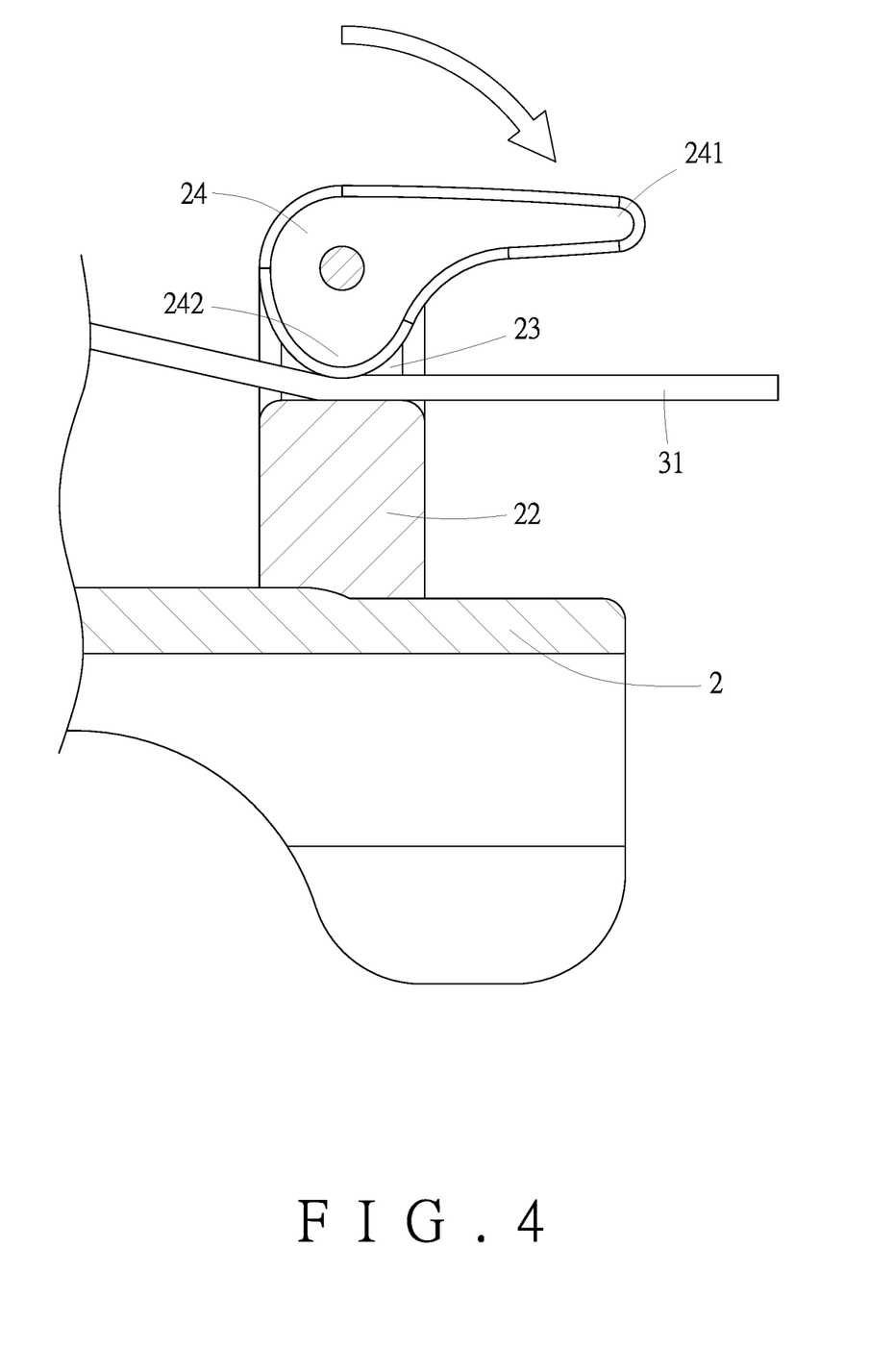
FIG. 4 is a schematic view illustrating that the elastic member is pressed and tightened by the pressing block according to the first embodiment of the present invention.

The tension adjustment unit (3) includes a plurality of elastic members (31). The elastic members (31) are elastic ropes. A first end of one of the elastic members (31) is directly fixed to the distal end of the thumb support rod (16). First ends of the other elastic members (31) are inserted through the perforations (151) of the finger support rods (15) and connected to the distal ends of the finger support rods (15), respectively. Second ends of the elastic members (31) pass through the pressing region (23) and are pressed and secured by the eccentric cam portions (242) of the pressing blocks (24), as shown in FIG. 4.

The joint unit (4) is a universal joint, which is connected between the palm orthosis body (1) and the forearm orthosis body (2). The palm orthosis body (1) can be turned an angle relative to the forearm orthosis body (2) through actuation of the joint unit (4). The angle is between −30° and +60°. The joint unit (4) includes a first actuating member (41), a second actuating member (42), and a lock nut (43). The first actuating member (41) is a ball head. The ball head is arranged on the first connecting portion (11) of the palm orthosis body (1). The second actuating member (42) is a ball socket. The ball socket is arranged on the second connecting portion (21) of the forearm orthosis body (2) for the ball head to be accommodated therein. The opening of the second actuating member (42) is provided with a threaded tightening portion (421). The periphery of the tightening portion (421) is formed with at least one slit (422) to increase the shrinkage allowance of the tightening portion (421) when it is tightened. The lock nut (43) is movably sleeved onto the first connecting portion (11) and is screwed to the tightening portion (421) to secure the ball head in the ball socket.

Figure 5:
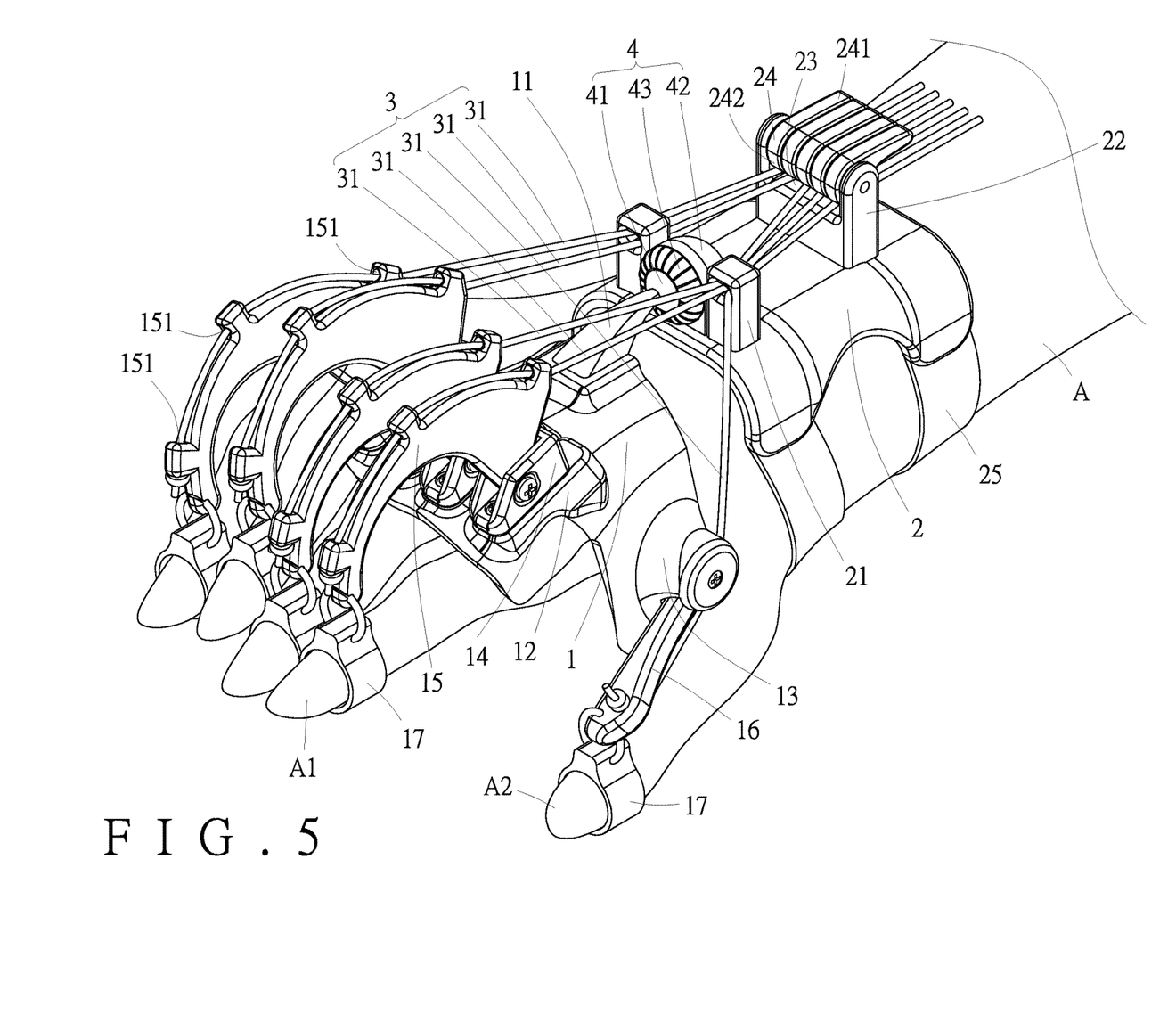
FIG. 5 is a schematic view according to the first embodiment of the present invention when in use.
Figure 6:
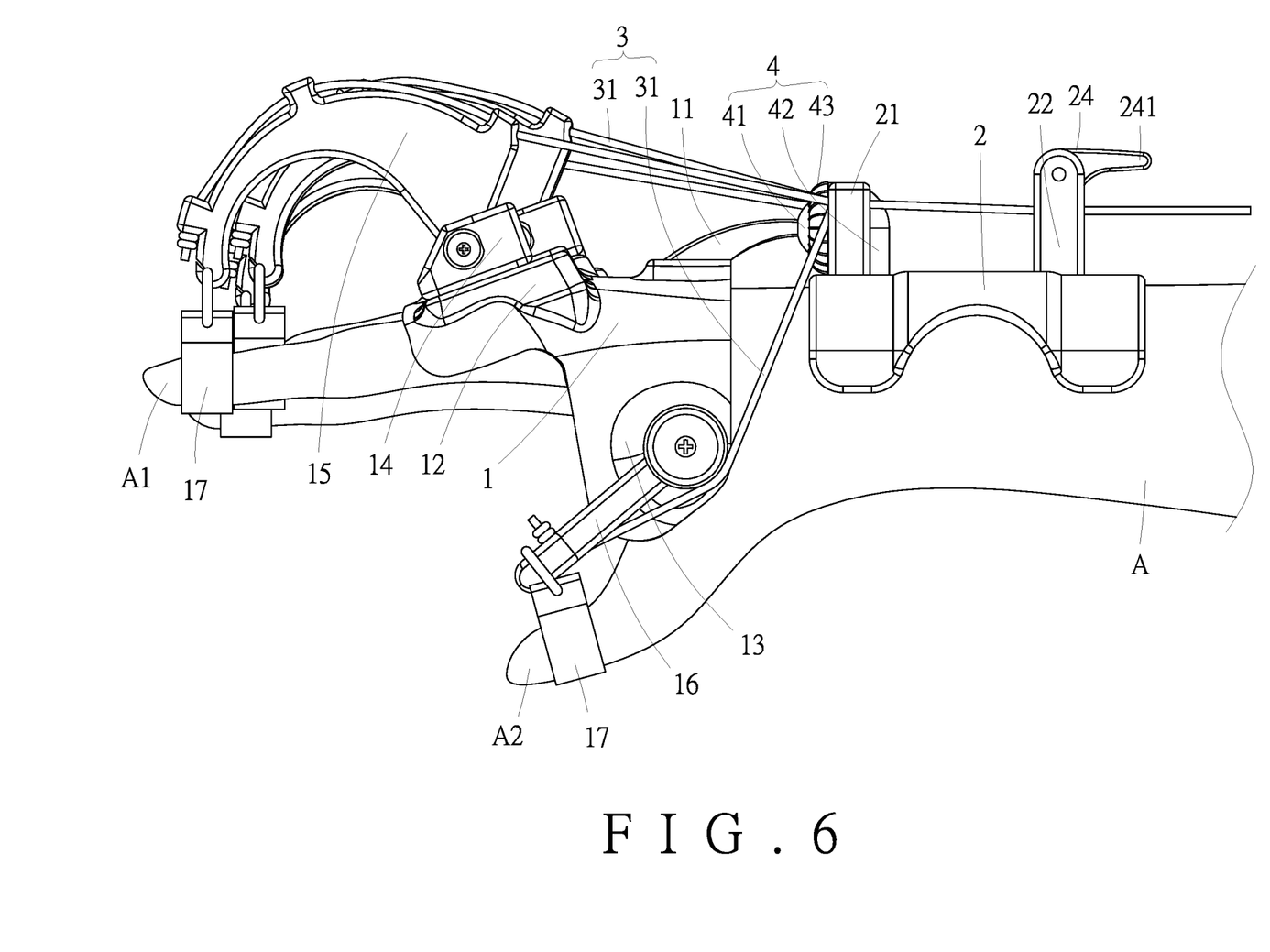
FIG. 6 is a side view according to the first embodiment of the present invention when in use.
Figure 7:
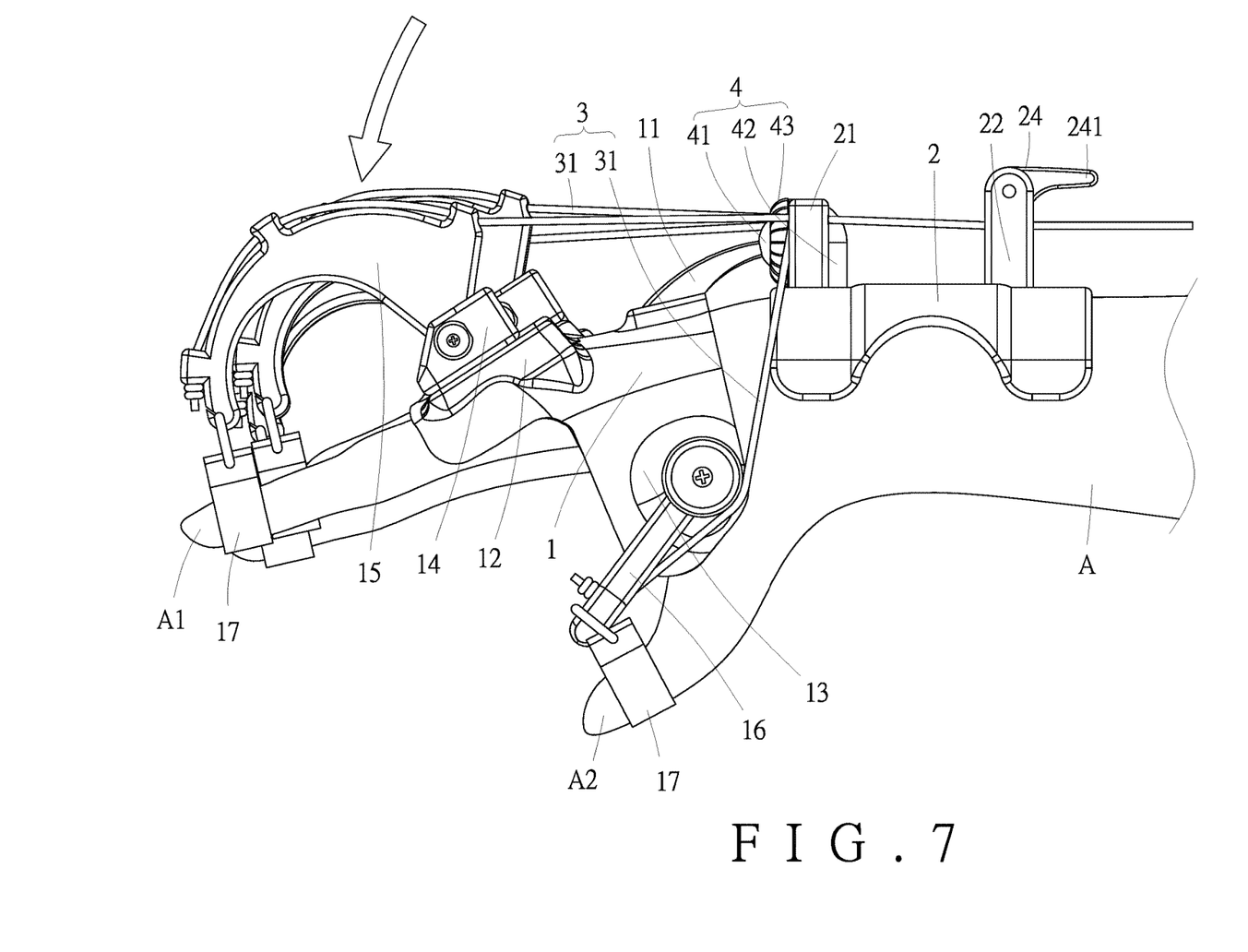
FIG. 7 is a schematic view illustrating the movement of the palm orthosis body relative to the forearm orthosis body according to the first embodiment of the present invention when in use.

When in use, as shown in FIG. 5 and FIG. 6, according to the different degree of bending of the wrist joint of a user, the lock nut (43) of the joint unit (4) is loosened so that it no longer tightens the tightening portion (421) of the second actuating member (42) as shown in FIG. 2. Then, the palm orthosis body (1) is adjustable relative to the forearm orthosis body (2), so that the first actuating member (41) is turned an appropriate angle relative to the second actuating (42), as shown in FIG. 7. The angle is between −30° and +60°. The hand rehabilitation device can be used according to the degree of bending of the user's wrist joint. When the adjustment is completed, the lock nut (43) is screwed to the tightening portion (421) again for securing the first actuating member (41) to the second actuating member (42). After that, the forearm orthosis body (2) is fitted onto a user's forearm (A) close to the wrist, and the fastening straps (25) on both sides of the forearm orthosis body (2) are wound around the forearm (A) and secured with the hook-and-loop tape (251) (as shown in FIG. 1), so that the forearm (A) is positioned in the forearm orthosis body (2). Then, the user's fingers (A1) and thumb (A2) are inserted and positioned in the finger sleeves (17) of the finger support rods (15) and the thumb support rod (16), respectively.

As shown in FIG. 5 and FIG. 6, when it is necessary to adjust the stretching tension for any one of the fingers (A1) or the thumb (A2), the corresponding pressing block (24) on the fixing seat (22) is slightly loosened. By pulling the pulling portion (241) of the corresponding pressing block (24), the corresponding eccentric cam portion (242) leaves the pressing region (23) (as shown in FIG. 3) and no longer presses the second end of the corresponding elastic member (31). According to the desired stretching tension for any one of the fingers (A1) or the thumb (A2), the corresponding elastic member (31) is selectively tightened or loosened by adjusting the length of the second end of the corresponding elastic member (31) to be pressed under the pressing block (24), so that the elasticity of the elastic member (31) pressed under the pressing block (24) can be adjusted. By tightening the second end of the elastic member (31), the corresponding finger (A1) is given a greater stretching tension. By loosening the second end of the elastic member (31), the corresponding finger (A1) is given a smaller stretching tension. After the stretching tension is adjusted, the pulling portion (241) is pulled to pivot the eccentric cam portion (242), such that the eccentric cam portion (242) is moved to the pressing region (23) (as shown in FIG. 4) to press and secure the second end of the elastic member (31). In this way, the elasticity of the respective elastic members (31) can be adjusted according to different stretching tensions required by the fingers (A1) or the thumb (A2) for rehabilitation.

Figure 8:
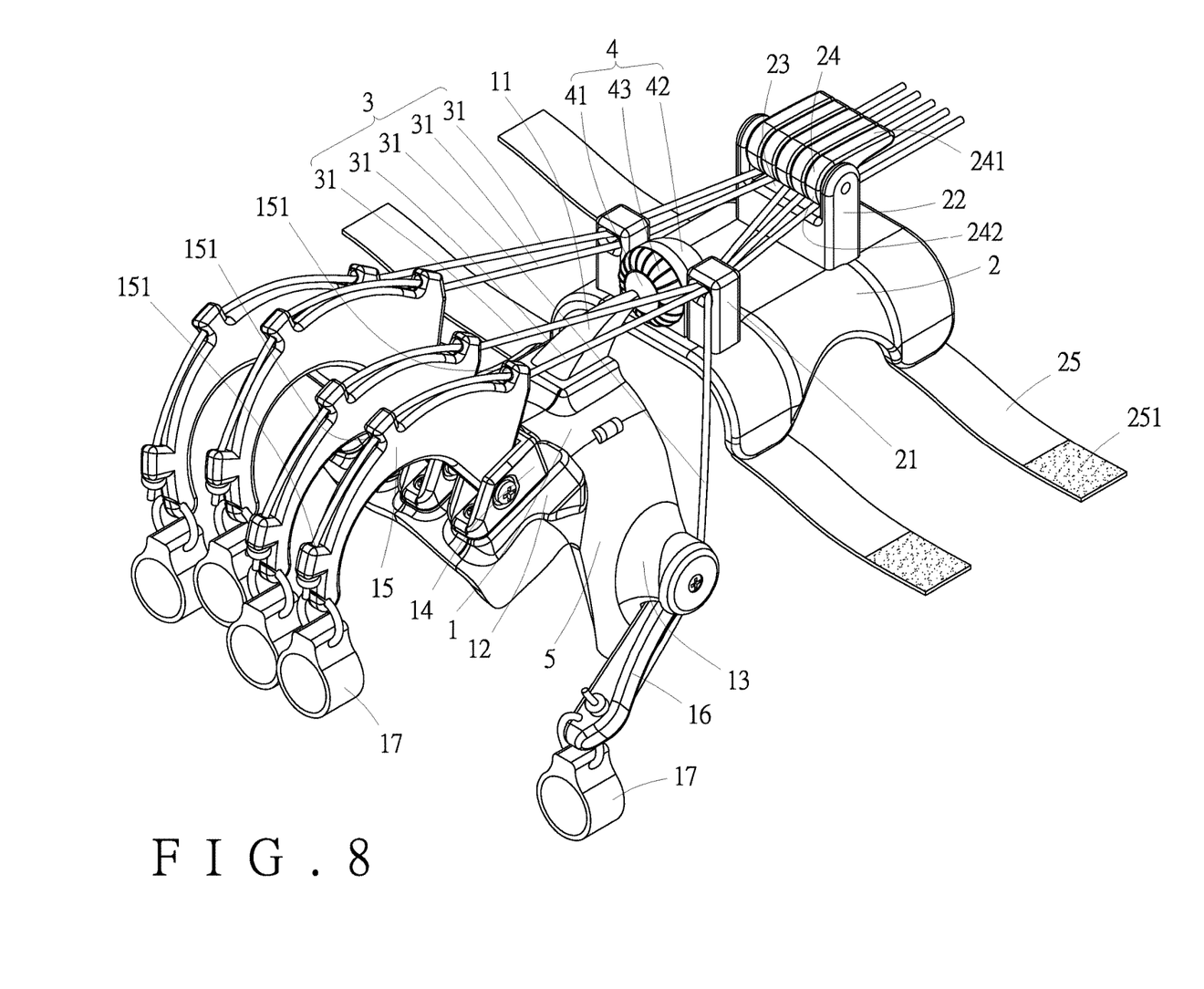
FIG. 8 is a perspective view according to a second embodiment of the present invention, wherein the swing plate is pivotally connected to the palm orthosis body.
Figure 9:
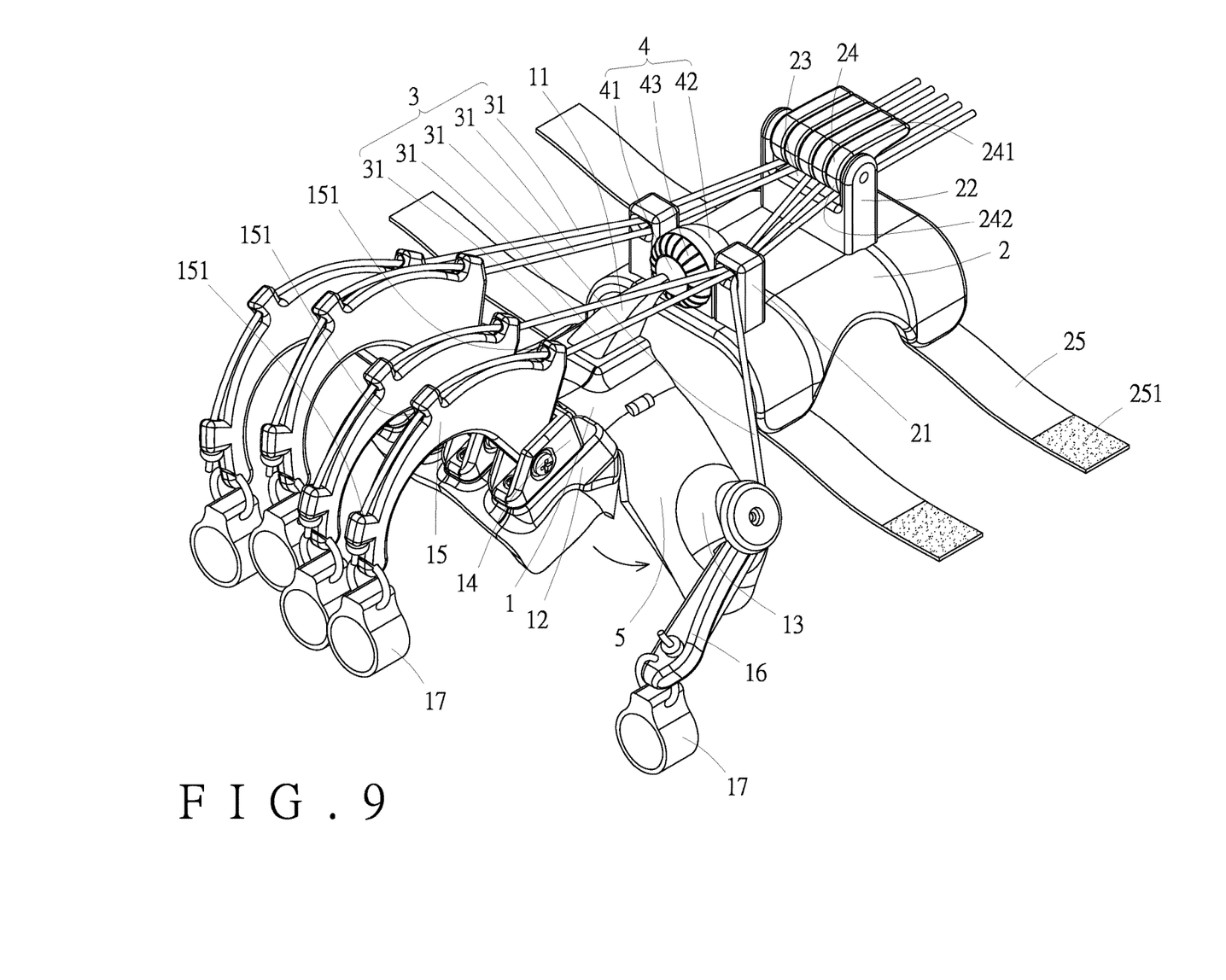
FIG. 9 is a schematic view according to the second embodiment of the present invention, illustrating that the swing plate is pivoted and swung relative to the palm orthosis body.

FIG. 8 illustrates a second embodiment of the present invention. A swing plate (5) is pivotally connected to one side of the palm orthosis body (1). The swing plate (5) is provided with the second fixing portion (13). The thumb support rod (16) is connected to the second fixing portion (13). As shown in FIG. 9, the swing plate (5) can be pivoted and swung relative to the palm orthosis body (1), so as to assist in training the thumb.

Although particular embodiments of the present invention have been described in detail for purposes of illustration, various modifications and enhancements may be made without departing from the spirit and scope of the present invention. Accordingly, the present invention is not to be limited except as by the appended claims.

What is claimed is:

1. A wrist joint actuating structure of a hand rehabilitation device, comprising:
a palm orthosis body, including a plurality of adjustable finger support rods, an adjustable thumb support rod, and a first connecting portion;
a forearm orthosis body, including a second connecting portion;
a joint unit, the joint unit being a universal joint and connected between the palm orthosis body and the forearm orthosis body, the joint unit including a first actuating member, a second actuating member and a lock nut, the first actuating member being arranged on the first connecting portion, the second actuating member being arranged on the second connecting portion, and the first actuating member being movable relative to the second actuating member, the first actuating member being a ball head, the second actuating member being a ball socket, an opening of the second actuating member being provided with a threaded tightening portion, wherein the lock nut is movably sleeved onto the first connecting portion and is screwed to the tightening portion to secure the ball head in the ball socket, and wherein the palm orthosis body can be turned an angle relative to the forearm orthosis body through actuation of the joint unit.

2. The wrist joint actuating structure of the hand rehabilitation device as claimed in claim 1, wherein a periphery of the tightening portion is formed with at least one slit to increase a shrinkage allowance of the tightening portion.

3. The wrist joint actuating structure of the hand rehabilitation device as claimed in claim 1, further comprising a tension adjustment unit, the forearm orthosis body further including a fixing seat, the tension adjustment unit including a plurality of elastic members, first ends of the plurality of elastic members being connected to the finger support rods and the thumb support rod respectively, second ends of the plurality of elastic members being secured to the fixing seat, the plurality of elastic members being adjustable to generate different stretching tensions by adjusting respective lengths of the second ends of the plurality of elastic members to be secured to the fixing seat.

4. The wrist joint actuating structure of the hand rehabilitation device as claimed in claim 3, wherein the fixing seat has a pressing region, the fixing seat is pivotally connected with a plurality of pressing blocks, each pressing block has a pulling portion and an eccentric cam portion, the pulling portion is pulled to pivot the eccentric cam portion so that the eccentric cam portion is moved to the pressing region for securing the second ends of the plurality of elastic members, the second ends of the plurality of elastic members can be adjusted for adjusting the respective lengths of the second ends of the plurality of elastic members to be pressed by the pressing blocks so as to generate the different stretching tensions.

5. The wrist joint actuating structure of the hand rehabilitation device as claimed in claim 3, wherein the finger support rods each have at least one perforation, and the first ends of the plurality of elastic members are inserted through the perforations of the finger support rods and connected to distal ends of the finger support rods, respectively.

6. The wrist joint actuating structure of the hand rehabilitation device as claimed in claim 1, wherein the angle is between −30° and +60°.

7. The wrist joint actuating structure of the hand rehabilitation device as claimed in claim 1, wherein the palm orthosis body is provided with a plurality of first fixing portions, a plurality of adjustment seats are connected to the first fixing portions respectively, the finger support rods are connected to the adjustment seats respectively, and finger sleeves are connected to the respective distal ends of the finger support rods.

8. The wrist joint actuating structure of the hand rehabilitation device as claimed in claim 1, wherein a swing plate is pivotally connected to one side of the palm orthosis body, the swing plate is provided with a second fixing portion, the thumb support rod is connected to the second fixing portion, and a finger sleeve is connected to a distal end of the thumb support rod.

* * * * *